United States Patent [19]

Barcza et al.

[11] 4,416,876
[45] Nov. 22, 1983

[54] PARA-AMINO BENZOIC AND PHENYLACETIC ACID DERIVATIVES

[75] Inventors: Sandor Barcza; Faizulla G. Kathawala, both of Mt. Lakes, N.J.

[73] Assignee: Sandoz, Inc., East Hanover, N.J.

[21] Appl. No.: 379,739

[22] Filed: May 19, 1982

[51] Int. Cl.³ ............................................. C07F 7/10
[52] U.S. Cl. .................................. 424/184; 556/410; 556/418
[58] Field of Search ................. 556/418, 410; 424/184

[56] References Cited

U.S. PATENT DOCUMENTS

| | | | |
|---|---|---|---|
| 3,513,184 | 5/1970 | Brison et al. | 556/418 |
| 3,517,041 | 6/1970 | Scharr et al. | 556/418 |
| 4,176,124 | 11/1979 | Darms et al. | 556/418 X |
| 4,281,145 | 7/1981 | Mitchell | 556/418 X |
| 4,339,581 | 7/1982 | Totten et al. | 556/418 X |

Primary Examiner—Paul F. Shaver
Attorney, Agent, or Firm—Gerald D. Sharkin; Richard E. Vila; Frederick H. Weinfeldt

[57] ABSTRACT

Compounds of the formula

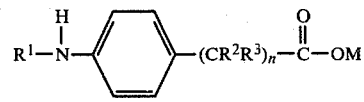

in which
  $R^1$ is a mono-silicon-containing hydrocarbyl radical having up to 35 carbon atoms;
  each of $R^2$ and $R^3$ is, independently, a hydrogen atom or lower alkyl having from 1 to 3 carbon atoms;
  n is 0 or 1; and
  M is a hydrogen atom, an equivalent of a cation which forms a non-toxic, pharmaceutically acceptable salt, or a non-toxic pharmaceutically acceptable monovalent radical which is hydrolyzable or saponifiable to an alkali metal cation, eg sodium 4-(4,4-dimethyl-4-sila-tetradecylamino)-benzoate, are useful as pharmaceutical agents.

35 Claims, No Drawings

PARA-AMINO BENZOIC AND PHENYLACETIC ACID DERIVATIVES

This invention relates to organic compounds, and more particularly to para-amino-benzoic and phenylacetic acid derivatives, the preparation thereof, and to the use of said compounds as pharmaceutical agents, as well as pharmaceutical compositions containing such compounds.

The compounds of this invention may conveniently be represented by formula I:

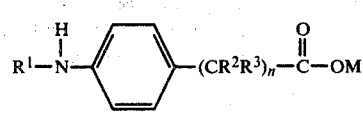

in which
R$^1$ is a mono-silicon-containing hydrocarbyl radical having up to 35 carbon atoms;
each of R$^2$ and R$^3$ is, independently, a hydrogen atom or lower alkyl having from 1 to 3 carbon atoms;
n is 0 or 1; and
M is a hydrogen atom, an equivalent of a cation which forms a non-toxic, pharmaceutically acceptable salt, or a non-toxic pharmaceutically acceptable monovalent radical which is hydrolyzable or saponifiable to an alkali metal cation.

Compounds I may be viewed as falling into 3 classes depending on the nature of M, ie (Ia) in which M=H; type (Ib) in which M=M', ie it is an equivalent of a cation; and (Ic) in which M=M'', ie it is a monovalent radical which is hydrolyzable to H or saponifiable to M'. Such hydrolyzable or saponifiable radicals are known in the art, and include lower alkyl, ie having from 1 to 6 carbon atoms, eg ethyl, benzyl, phenyl or 3-nicotinyl; the alkyl or aryl carbon atoms of which may be unsubstituted or substituted by at least one fluoro, chloro or bromo, lower alkyl (having up to 3 carbons), lower alkoxy (having up to 3 carbons) or a carboxy unit. R$^1$ is preferably a hydrocarbyl radical interrupted by a single quarternary silicon atom in a saturated linear segment thereof, said hydrocarbyl radical having up to 35 carbon atoms.

Subclasses of Compounds I include those in which R$^1$ has the structure A:

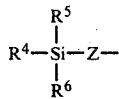

wherein each of R$^4$, R$^5$ and R$^6$ is, independently,
(a) alkyl having from 1 to 20 carbon atoms; or
(b) of the formula

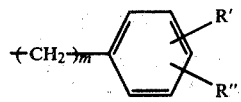

in which m is 0, 1 or 2, and each of R' and R'' is independently a hydrogen atom, alkyl having from 1 to 3 carbon atoms, alkoxy having from 1 to 3 carbon atoms, or halo having an atomic weight of from about 18 to 127; and Z is a divalent hydrocarbyl radical having from 1 to 20 carbon atoms, selected from the group consisting of (1) alkylene, (2) cycloalkylidene (having from 5 to 12 ring carbons), or (3) aralkylidene (the aryl portion being either a phenyl or naphthyl ring, which may be substituted by 1 or 2 alkyl groups having from 1 to 3 carbon atoms); or R$^1$ is the structure (B):

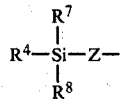

in which Z and R$^4$ are as defined above, and R$^7$ and R$^8$ are saturated hydrocarbyl radicals joined to form a cyclic structure having from 3 to 20 carbon atoms as ring members, preferably from 4 to 7 ring carbon atoms, and may have one or two lower alkyl substituents of from 1 to 3 carbon atoms.

Particular preferences in compounds I, are those having one or more of the following characteristics:
(1) R' is of structure type A in which R$^4$, R$^5$ and R$^6$ are each alkyl of from 1 to 20 carbon atoms with R$^5$ and R$^6$ preferably being the same alkyl having from 1 to 3 carbon atoms, e.g. methyl; (2) Z is of the structure Z':

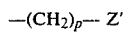

in which p is a whole number of from 1 to 6, e.g. 2, 3, 4 or 5; (3) n is 0; and (4) M is hydrogen or an alkali metal cation. Among the above stated preferences it is generally more preferred that: (1) R$^4$ is alkyl of 8 to 20 carbon atoms, especially 8 to 12 carbon atoms, particularly unbranched alkyl, e.g. n-decyl; (2) M is an alkali metal, especially sodium; and (3) the total carbon atoms in Z' and R$^4$ is from 9 to 19, particularly 13 to 15.

Compounds Ic (ie the ester forms of I) are obtainable by reacting an ester of the formula II:

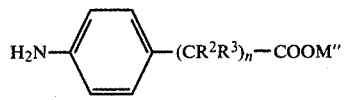

in which R$^2$, R$^3$ and n are as defined above and M'' is as defined above eg ethyl; with a silicon-bearing hydrocarbyl radical-contributing compound of the formula III:

in which R$^1$ is as defined above and L is a leaving group, eg iodo, or a sulfonyloxy unit, such as p-toluene sulfonyloxy, (process a). Process (a) may conveniently be carried out by reacting compounds II and III at from ambient to elevated temperatures, eg at from about 20° to 160°, preferably at from about 120° to 130° C. While excess of a reactant may serve as the reaction medium, if liquid under the reaction conditions, if desired an inert medium may be employed eg a hydrocarbon such as toluene, xylene or octane or a high-boiling ether such as dimethoxyethane or dioxane. Preferably the medium is an aprotic non-nucleophilic polar solvent. It is preferred to carry out process (a) in an atmosphere of dry nitrogen.

Compounds II and III are generally known in the art, and those that are not known may be prepared by methods analogous to those disclosed in the literature for preparing the known compounds.

Chemical functions which can serve as a leaving group (L) are known in the literature, as are methods for preparation of compounds bearing such functions eg U.S. Pat. No. 3,969,415. Functions suitable as L- include (a) arylsulfonyloxy in which the aryl group is phenyl or naphthyl which may be unsubstituted, or mono- or disubstituted by alkyl of 1 to 6 carbon atoms, eg methyl, alkoxy of 1 to 6 carbon atoms, nitro, or halogen (F, Cl, or Br); (b) halogens, e.g., fluoro, chloro, bromo or iodo; (c) alkylsulfonyloxy in which the alkyl group may be substituted, e.g. halogen or unsubstituted and contain from 1 to as many as 16 or more, preferably 1 to 6, carbon atoms, e.g. methane sulfonyloxy, ethanesulfonyloxy, 3-chloropropanesulfonyloxy, or 1-hexadecanesulfonyloxy; and (d) esters of strong acids, eg trifluoromethane sulfonates or perfluoroalkanoates. The term halogen with respect to L, is intended to include F, Cl, Br and I.

A particularly convenient method for preparing compounds III in which L is an arylsulfonyloxy (process b) is by reacting an alcohol compound of formula IV:

$$R^1\text{---}OH \qquad \qquad IV$$

in which $R^1$ is as defined above, with a corresponding arylsulfonyl halide, eg the chloride, in the presence of an acid acceptor, eg a tertiary amine, such as pyridine (an excess of which can also serve as reaction medium), at moderate temperatures, eg from about 0° to +20° C., particularly from about +5° to +12° C.

Compounds IV', ie compounds IV in which the terminal carbon of $R^1$ is a methylene unit, may be obtained by reducing corresponding carboxylic acids or esters of the formula V:

$$R^{1'}\text{---}COOR^e \rightarrow R^{1'}\text{---}CH_2\text{---}OH \text{ (IV')} \qquad (V)$$

in which $R^{1'}$ is the residue of $R^1$ when the terminal methylene unit has been removed, and $R^e$ is a hydrogen atom or lower alkyl (having up to 4 carbon atoms, eg methyl or ethyl. The reduction step (process c) may be carried out by conventional means, for example by employing lithium aluminum hydride in tetrahydrofuran.

Methods of preparing various intermediates eg compounds IV, and V, (or analogs thereof) are described in U.S. Pat. No. 4,297,349 and corresponding European patent.

The various forms of Compounds I with respect to M can be readily interconverted, by methods known in the art. For example, a compound Ic (obtained by process a) can be saponified to its corresponding salt form (Ib) which can be acidified to its corresponding free acid (Ia) which can, alternatively be reacted with a suitable base to obtain the corresponding salt form (Ib) or esterified to a compound Ic.

While process (a) is described above employing an ester (II), the process may be carried out analogously employing analogs of compounds II in which H or M' replaces M", if so desired.

A particularly convenient method of preparing compounds Ia, ie compounds I in which M is a hydrogen, (process a') involves reacting a compound III in the manner described above for process (a), but with a reagent of formula II':

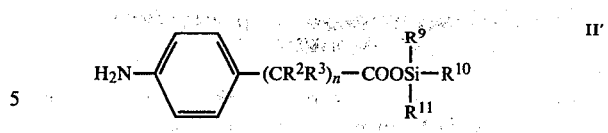

in which $R^2$, $R^3$ and n are as defined above; and in which each of $R^9$, $R^{10}$ and $R^{11}$ is, independently, alkyl or alkenyl having from 1 to 8 carbon atoms, or phenyl; preferably lower alkyl of from 1 to 4 carbon atoms, and more preferably each is methyl, in place of a compound II, to obtain an intermediate which is readily hydrolyzed to the corresponding compound Ia.

Compounds II' are obtainable by conventional silylation techniques, for example by treatment of a compound VI

in which $R^9$, $R^{10}$ and $R^{11}$ are as defined above, and X is chloro, bromo, or iodo, or other leaving group, e.g. triflate or perchlorate, preferably chloro; with an analog of a compound II in which M" is replaced by H, a compound II":

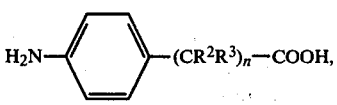

in which $R^2$ and $R^3$ and n are as defined above, under essentially anhydrous conditions, in the presence of an acid acceptor e.g. triethylamine in an inert solvent, e.g. dichloromethane at a temperature of from about 0° to 60° C. (preferably at about 10° to 20° C.).

The hydrolyzable immediate product of process (a') is believed to be of the formula Ia':

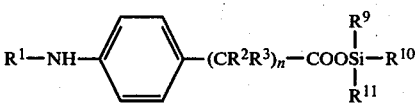

in which $R^2$, $R^3$, $R^9$, $R^{10}$, $R^{11}$, $R^1$ and n are as defined above. However, upon exposure to moisture during recovery, the intermediate Ia' hydrolyzes to yield the "free acid form", i.e. the corresponding compound Ia; hence is not recovered per se.

The products of the processes described herein may be recovered and refined, where such is desired, by conventional means, such as by crystallization, distillation or chromatographic techniques such as column or thin layer chromatography.

STATEMENT OF UTILITY

The compounds of the formula I are useful as agents in the treatment and prophylaxis of atherosclerosis as indicated by a lowering of serum total cholesterol, and/or serum triglyceride levels in mammals.

The activity of compounds I in lowering serum total cholesterol, and/or serum triglyceride levels is indicated in feeding tests on laboratory rats in which groups of male Wistar Royal Hart rats, weighing from 160 to 180 g, which have been fed ground Purina Rat Chow for one week are placed 2 per cage, using 6 rats per treatment. Drugs are incorporated into the powdered diet by first mixing the drug in a small amount of diet in a Wareing Blender and then mixing with sufficient diet to make 1 kilo. Weights of the rats and food hoppers are recorded at the beginning and end of the study to monitor weight gain and food consumption.

At the end of 6 days on drug, the rats are anesthetized with hexobarbital and blood samples are obtained by making a carotid incision and the blood is collected in acid washed tubes. Internal organs are inspected for any abnormalities and liver excised, weighed and frozen for lipid analyses. After clotting at room temperature, the blood samples are centrifuged to separate the serum. The serum is transferred to clear acid washed tubes for analysis of the total cholesterol, triglycerides and lipoprotein fractions.

Lipoproteins are fractionated on density adjusted serum using an ultracentrifuge into low density lipoprotein (LDL—includes chylomicra and VLDL) and high density lipoproteins (HDL). Total serum cholesterol, LDL and HDL cholesterol are analyzed using the Auto Analyzer II Method No. 339-26 by altering the pump tubing size to obtain greater sensitivity (micro modification). Serum triglycerides are analyzed using the Auto-Analyzer II Method No. 339-12 modified by altering the pump tubing size for greater sensitivity.

Carrying out the above-described test using sodium 4-(4,4-dimethyl-4-sila-n-tetradecylamino)-benzoate (product of Example 9c) as test compound, at various levels, the results presented in table I, below, are obtained:

TABLE I

| Dose | | % decrease from control | | | |
|---|---|---|---|---|---|
| % diet | mg/kg/ day | Cholesterol Total | Cholesterol VLDL + LDL | HDL | triglycerides |
| .25 | 250 | 51 | 79 | 48 | 76 |
| .12 | 120 | 24 | 33 | 30 | 64 |
| .06 | 60 | 12 | 18 | 9 | 52 |

Carrying out the above-described test using other compounds I (at a level of 0.25% of diet, the results presented in Table II below are obtained:

TABLE II

| Cmpd. of Ex. | Dose % In Diet | Dose mg/kg/ day | % change from control Cholesterol Total | % change from control Cholesterol VLDL + LDL | % change from control Cholesterol HDL | Triglycerides |
|---|---|---|---|---|---|---|
| 3 | .25 | — | 44 ↓ | 75 ↓ | 37 ↓ | 60 ↓ |
| 5* | .25 | — | 30 ↓ | 21 ↓ | 0 | 75 ↓ |
| 9b | .25 | — | 37 ↓ | 71 ↓ | 22 ↓ | 64 ↓ |
| 9f | .25 | 288 | 13 ↑ | 50 ↓ | 32 ↑ | 86 ↓ |
| 9g | .25 | 244 | 14 ↑ | 18 ↓ | 4 ↑ | 80 ↓ |
| 9h | .25 | 286 | 2 ↑ | 12 ↓ | 10 ↓ | 68 ↓ |

*sodium salt form

In addition to the above-mentioned activity, the compound of Example 9c is also indicated as agent useful in the treatment or prevention of atherosclerosis as indicated by an ability to control the cholesterol ester content of mammalian cells, such as those in the mammalian arterial wall, as demonstrated by known test procedures in which the visual observation of cytoplasmic inclusions which have been shown to be directly correlated with the total cholesterol ester content of cultured cells is shown to be reduced by a test compound, as compared to untreated cells, and carried out, for example by the following procedure:

Cell Culture Procedure

Stock monolayer cultures of the Fu5AH rat hepatoma cell line (Rothblat, G. H., *Lipids,* 9, 526-535, 1974) are routinely maintained in Eagle's Minimum Essential Medium (EMEM) supplemented with 10% fetal bovine serum (FBS) in 75 cm$^2$ tissue culture flasks. For this study, when the cultures reached confluence, they are removed by mild enzymatic treatment with 0.25% trypsin in Hanks' balanced salt solution (without calcium and magnesium). After centrifugation of the cell suspension and aspiration of the enzymatic solution, the cell pellet is resuspended in an appropriate volume of media for seeding into 60 mm tissue culture dishes. The cultures are incubated at 37° C. in an atmosphere of high humidity and 5% $CO_2$. When the cultures are one-half to two-thirds confluent (approximately 5 days) they are ready for use. Test compounds are solubilized in dimethyl sulfoxide (DMSO). The culture dishes are randomly divided into the following groups.

Normal Control: 5 ml EMEM with 10% FBS.
Hyperlipemic Control: 5 ml EMEM with 10% FBS to which was added 5% hyperlipemic rabbit serum (HRS) containing≃1500 mg/dl total cholesterol plus 0.05 ml DMSO.
Test Groups: Same as Control plus 0.05 ml of test compounds at a concentration of 1 mg/ml DMSO to yield a final concentration of 10 μg/ml.

The cultures are returned to the incubator for 24 hours. At the end of this time period, the cells are examined microscopically with an inverted phase contrast microscope. Notations are made regarding the condition of the cells (cytotoxicity) and any alterations in the shape, size or number of lipid inclusions relative to the control and standard. A qualitative assessment of inclusions in test compound treated group relative to control and standard is made, re, (1) no drug effect;
(2) reduced number of inclusions <, =, > standard.

When the compounds are employed for the above usage, they may be combined with one or more pharmaceutically acceptable carriers, e.g., solvents, diluents and the like, and may be administered orally in such forms as tablets, capsules, dispersible powders, granules, suspensions containing, for example, from about 0.5 to 5% of suspending agent, syrups containing, for example, from about 10 to 50% of sugar, and elixirs containing, for example, from about 20 to 50% ethanol, and the like. These pharmaceutical preparations may contain, for example, from about 0.5% up to about 90% of the active ingredient in combination with the carrier, more usually between 5% and 60% by weight.

The antiatherosclerotic effective dosage of active ingredient employed may vary depending on the particular compound employed, the mode of administration and the severity of the condition being treated. However, in general, satisfactory results are obtained when the compounds of formula I are administered orally at a daily dosage of from about 5 milligrams to about 250 milligrams per kilogram of animal body weight, preferably given in divided doses two to four times a day, or in sustained release form. For most large mammals, the total daily dosage is from about 350 milligrams to about 5,000 milligrams. Dosage forms suitable for internal (ingestion) use comprise from about 100 to 2,500 milligrams of the active compound in intimate admixture with a solid or liquid pharmaceutically acceptable carrier. Solid carriers include starch, lactose and kaolin, while liquid carriers include sterile water, polyethylene glycols and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants eg vitamine E, ascorbic acid, BHT and BHA.

The preferred pharmaceutical compositions from the stand-point of each of preparation and administration are solid compositions, particularly tablets and hard-filled or liquid-filled capsules. Where the carrier is a liquid, it is preferably an edible oil. Also preferred as liquid carriers are those in which water is not a major component, and particularly in which water is essentially absent.

A representative formulation for administration orally three times a day in the treatment of atherosclerosis is a gelatin capsule prepared by conventional techniques to contain the following

| Ingredient | Weight (in Mg.) |
|---|---|
| sodium 4-(4,4-dimethyl-4-sila-n-tetradecylamino)-benzoate | 300 |
| lactose | 200 |

Examples are presented hereinafter as illustrative of the preparation of compounds of this invention. All temperatures are centigrade and room temperature is 20° to 30° C., unless indicated otherwise.

EXAMPLE 1

Ethyl 4-(4,4-dimethyl-4-sila-n-hexadecylamino)-benzoate

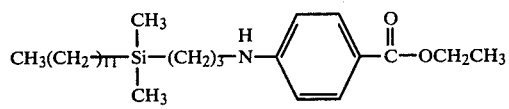

Step A, 1-(4,4-dimethyl-4-sila-n-hexadecyl)-p-toluenesulphonate

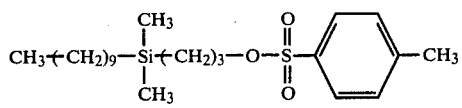

A solution of 16.0 g (55.9 mmol) of 4,4-dimethyl-4-sila-n-hexadecan-1-ol in 10 ml of pyridine is added, with stirring, to a solution of 16.8 g (88.2 mmol) of p-toluenesulphonyl chloride in 30 ml of pyridine in a vessel with ice-bath cooling to maintain the temperature in the vessel at +8° to 12°. Stirring is continued for 3 hrs. A further charge of 6.9 g (36.2 mmol) of p-toluenesulphonyl chloride is added, with stirring, and stirring continued (at +5° to 12° in the vessel) for 2 hrs. The reaction mixture is then poured into ice-water, and extracted with ethyl acetate-diethyl ether (1/1). The organic layer is washed thrice with portions of 2 N hydrochloric acid, once with saturated aqueous sodium bicarbonate solution, and once with saturated aqueous sodium chloride (brine), the organic phase dried over anhydrous sodium sulfate, filtered and the filtrate concentrated in vacuo at from about 10°-30° to obtain the title product of this step as an oil (which freezes at −20°). This product should be used promptly in the next step, or stored frozen until used.

Step B

Ethyl-4-(4,4-dimethyl-4-sila-n-hexadecylamino)benzoate

Under nitrogen, 26.8 g of 4,4-dimethyl-4-sila-n-hexadecyl-p-toluenesulphonate, mixed with 35 g (in excess) of ethyl-p-aminobenzoate is heated at 123° to 128° for 4 hrs. The hot mixture is diluted with about 120 ml. of toluene and allowed to cool. The solution is then further diluted with dichloromethane. The resulting mixture is then washed with about 50 ml. of dilute aqueous sodium hydroxide, then washed with brine, and then dried over anh. sodium sulfate, filtered, and the filtrate concentrated by evaporating to obtain an oily residue. Heptane is added to the residue and upon standing two crops of solids (ethyl-p-aminobenzoate) are removed by filtering. The filtrate is concentrated to give an oily product which is placed on a chromatographic column, eluted with ethyl acetate/dichloromethane (5/95) to obtain several high quality fractions, which upon recrystallization from heptane, cooling to −20° gives refined title product, m.p. (39)—40°-41°. Additional crops of product are obtained from other fractions.

EXAMPLE 2

4-(4,4-Dimethyl-4-sila-n-hexadecylamino)-benzoic acid

To 11.50 g (26.5 mmol) of ethyl-4-(4,4-dimethyl-4-sila-n-hexadecylamino)-benzoate in 150 ml of freshly distilled 2-methoxy-ethanol (peroxide free) refluxing under nitrogen, is gradually added a solution of 10.0 g (approx. 161 mmol) of potassium hydroxide in 17 ml of water. After the addition, refluxing is continued for 45 mins. Then 15 ml (250 mmol) of acetic acid (100%) is added and the reaction mixture cooled. Toluene is then added and the mixture agitated. The organic phase is recovered, washed with 4 portions of water, dried over anh. sodium sulfate, filtered and the filtrate evaporated to yield crude title product as a semi-solid residue, which upon recrystallization from heptane-hexane (50/50) gives refined title product, m.p. (88)—89°-90°.

EXAMPLE 3

Sodium 4-(4,4-dimethyl-4-sila-n-hexadecylamino)-benzoate

To a solution of 6.79 g (16.7 mmol) of 4-(4,4-dimethyl-4-sila-hexadecylamino)benzoic acid in 10 ml of ethanol is added an aqueous solution of 1.5 g (17.8 mmol) of sodium bicarbonate (in about 50 ml of water). The mixture is heated to 60° and the resultant clear solution evaporated, under vacuum, to obtain the title product as a white crystalline solid, m.p. above 300°.

EXAMPLE 4

Ethyl 4-(6,6-Dimethyl-6-sila-n-hexadecylamino)-benzoate

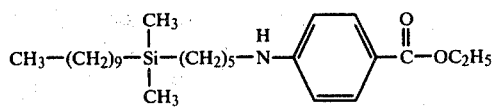

Step A

6,6-dimethyl-6-sila-hexadecan-1-ol $CH_3-(CH_2)_9-Si(CH_3)_2-(CH_2)_5-OH$

Under nitrogen, 17.1 g (56.9 mmol) of 6,6-dimethyl-6-sila-n-hexadecanoic acid, dissolved in 20 ml of absolute tetrahydrofuran, is added dropwise to 5.4 g (142 mmol) of lithium aluminum hydride in 150 ml of absolute tetrahydrofuran (caution being exercised due to hydrogen evolution). The resultant mixture is stirred at 60° for 18 hrs., then cooled to about 10°; and injected into a cold (about 10°) saturated aqueous of sodium-potassium tartrate. Dichloromethane is added and the mixture acidified with dilute hydrochloric acid (2 N). The organic phase is separated, washed with saturated aqueous sodium bicarbonate solution, then dried over anh. sodium sulfate, filtered and the filtrate concentrated to obtain the crude title product of this step as an oily residue. The oily residue is distilled in a kugelrohr apparatus and the fraction collecting at 108° to 115° and 0.19 to 0.13 mm Hg to obtain refined title product of this step.

Steps B and C

Ethyl 4-(6,6-dimethyl-6-sila-n-hexadecylamino benzoate.

Following the procedure of Step A of Example 1, 1-(6,6-dimethyl-6-sila-hexadecyl)-p-toluenesulfonate is prepared, which is reacted with ethyl p-aminobenzoate, following the procedure of Step B of Example 1 to obtain the title product of the example, m.p. (42)—43°-44°.

EXAMPLE 5

Following the procedure of Example 2, the free acid of the product of Example 4 is obtained, m.p. (79)—79.5°-80°, which upon treatment according to the procedure of Example 3 yields the sodium salt thereof (m.p. above 300°).

EXAMPLE 6

Ethyl 4-(4,4-dimethyl-4-sila-hexadecylamino)phenylacetate

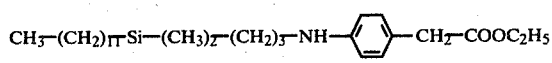

Repeating the procedure of Example 1, but using in place of the ethyl p-aminobenzoate used therein, an approximately equivalent amount of ethyl p-aminophenylacetate there is accordingly obtained the title product.

EXAMPLE 7

Repeating the procedure of Example 1, but using in place of the 4,4-dimethyl-4-sila-n-hexadecan-1-ol used therein, an approximately equivalent amount of:
(a) 6,6-diethyl-6-sila-n-hexadecan-1-ol;
(b) 5,5-dimethyl-5-sila-n-hexadecan-1-ol;
(c) 4,4-dimethyl-4-sila-n-tetradecan-1-ol;
(d) 4,4-diphenyl-4-sila-n-octan-1-ol;
(e) 4-(4,4-dimethyl-4-sila-n-decyl)-cyclohexanol;
(f) 4,4-diphenyl-4-sila-n-pentan-1-ol;
(g) 4-phenyl,4-methyl-4-sila-n-pentan-1-ol; or
(h) 4-(4-phenoxyphenyl),4-methyl-4-sila-n-pentan-ol;
there is accordingly obtained (Compounds Ic):
(a) ethyl 4-(6,6-diethyl-6-sila-n-hexadecylamino)benzoate;
(b) ethyl 4-(5,5-dimethyl-5-sila-n-hexadecylamino)-benzoate, m.p. (87) 87.5°-89°;
(c) ethyl 4-(4,4-dimethyl-4-sila-n-tetradecylamino)-benzoate, m.p. (87) 88°-89°;
(d) ethyl 4-(4,4-diphenyl-4-sila-n-octylamino)benzoate;
(e) ethyl 4-[4-(4,4-dimethyl-4-sila-n-decyl)-cyclohexyl amino]-benzoate;
(f) ethyl 4-(4,4-diphenyl-4-sila-n-pentylamino)benzoate;
(g) ethyl 4-(4-phenyl,4-methyl-4-sila-n-pentylamino)-benzoate; and
(h) ethyl 4-(4-phenoxyphenyl),4-methyl-4-sila-n-pentylamino)benzoate.

EXAMPLE 8

Repeating the procedure of Example 2 using an approximately equivalent amount of each of the compounds (Ic) of Examples 7 and 6 there is accordingly obtained the corresponding free acids (Ia) thereof, namely:
(a) 4-(6,6-diethyl-6-sila-n-hexadecylamino)-benzoic acid;
(b) 4-(5,5-dimethyl-5-sila-n-hexadecylamino)-benzoic acid, m.p. (52) 54°-56°;
(c) 4-(4,4-dimethyl-4-sila-n-tetradecylamino)benzoic acid, m.p. (86) 86.5°-87°;
(d) 4-(4,4-diphenyl-4-sila-n-octylamino)-benzoic acid;
(e) 4-[4-(4,4-dimethyl-4-sila-n-decyl)-cyclohexanyl amino]-benzoic acid;
(f) 4-(4,4-diphenyl-4-sila-n-pentylamino)-benzoic acid, m.p. (125)—126°-127°;
(g) 4-(4-phenyl-4-methyl-4-sila-n-pentylamino)-benzoic acid m.p. (108)—112°-113°;
(h) 4-(4-phenoxyphenyl-4-methyl-4-sila-n-pentylamino)benzoic acid m.p. (125)—125.5°-126.5°;
(i) p-(4,4-dimethyl-4-sila-n-hexadecylamino)-phenylacetic acid,

EXAMPLE 9

Repeating the procedure of Example 3 but using in place of the 4-(4,4-dimethyl-4-sila-n-hexadecylaminobenzoic acid used therein, an approximately equivalent amount of each of the compounds of Example 8, the corresponding sodium salts thereof are obtained (Compounds Ib), namely:
(a) sodium 4-(6,6-diethyl-6-sila-n-hexadecylamino)-benzoate; m.p. over 300°;
(b) sodium 4-(5,5-dimethyl-5-sila-n-hexadecylamino)-benzoate, m.p. above 300°;
(c) sodium 4-(4,4-dimethyl-4-sila-n-tetradecylamino)-benzoate; m.p. above 300°;

(d) sodium 4-(4,4-diphenyl-4-sila-n-octylamino)benzoate;
(e) sodium 4-[4(4,4-dimethyl-4-sila-n-decyl)-cyclohexyl amino]-benzoate;
(f) sodium 4-(4,4-diphenyl-4-sila-n-pentylamino)benzoate, m.p. 280(d);
(g) sodium 4-(4-phenyl-4-methyl-4-sila-n-pentylamino)benzoate, m.p. (142)—168°-290°(d);
(h) sodium 4-(4-phenoxyphenyl-4-methyl-4-sila-n-pentylamino)-benzoate (glassy) m.p. (78)—83°-200°;
(i) sodium p-(4,4-dimethyl-4-sila-n-hexadecylamino)-phenylacetate.

EXAMPLE 10

Compounds of Example 8f, 8g and 8h are prepared by the method of Example 1, except that appropriate reagents II' (in which $R^9=R^{10}=R^{11}=$methyl) are used in place of reagents II, in equivalent amounts.

What is claimed is:
1. A compound of the formula:

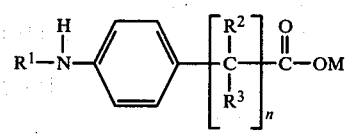

in which
$R^1$ is a mono-silicon-containing hydrocarbyl radical having up to 35 carbon atoms;
each of $R^2$ and $R^3$ is, independently, a hydrogen atom or lower alkyl having from 1 to 3 carbon atoms; n is 0 or 1; and
M is a hydrogen atom, an equivalent of a cation which forms a non-toxic, pharmaceutically acceptable salt, or a non-toxic, pharmaceutically-acceptable monovalent radical which is hydrolyzable or saponifiable to an alkali metal cation.

2. A compound of claim 1, in which $R^1$ is a radical of the formula:

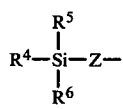

wherein each of $R^4$, $R^5$ and $R^6$ is, independently,
(a) alkyl having from 1 to 20 carbon atoms; or
(b) of the formula

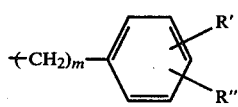

in which m is 0, 1 or 2; each of R' and R" is independently a hydrogen atom, alkyl having from 1 to 3 carbon atoms, alkoxy having from 1 to 3 carbon atoms, or halo having an atomic weight of from about 18 to 127; and Z is a divalent hydrocarbyl radical having from 1 to 20 carbon atoms, selected from the group consisting of (1) alkylene, (2) cycloalkylidene having from 5 to 12 ring carbons, or (3) aralkylidene in which the aryl portion is either a phenyl or naphthyl ring, which may be unsubstituted or substituted by one or two alkyls having from 1 to 3 carbon atoms.

3. A compound of claim 2 in which each of $R^4$, $R^5$ and $R^6$ is of type (a).
4. A compound of claim 2 in which at least one of $R^4$, $R^5$ and $R^6$ is of type (b).
5. A compound of claim 3 in which $R^5$ is alkyl having from 1 to 3 carbon atoms, and $R^6$ is the same as $R^5$.
6. A compound of claim 5 in which $R^4$ has from 8 to 20 carbon atoms.
7. A compound of claim 5 in which $R^4$ has from 8 to 12 carbon atoms, and is unbranched.
8. A compound of claim 7 in which $R^4$ is n-decyl.
9. A compound of claim 4 in which n is 0.
10. A compound of claim 1 in which $R^1$ is a radical of the formula:

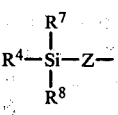

wherein $R^4$ is (a) alkyl having from 1 to 20 carbon atoms; or (b) of the formula

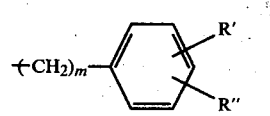

in which m is 0, 1 or 2; each of R' and R" is independently a hydrogen atom, alkyl having from 1 to 3 carbon atoms, alkoxy having from 1 to 3 carbon atoms, or halo having an atomic weight of from about 18 to 127; and Z is a divalent hydrocarbyl radical having from 1 to 20 carbon atoms, selected from the group consisting of (1) alkylene, (2) cycloalkylidene having from 5 to 12 ring carbons, or (3) aralkylidene in which the aryl portion is either a phenyl or naphthyl ring, which may be unsubstituted or substituted by one or two alkyls having from 1 to 3 carbon atoms and $R^7$ and $R^8$ are hydrocarbyl radicals which are joined to form a cyclic structure having from 3 to 20 carbon atoms as ring members.

11. A compound of claim 10 in which $R^7$ and $R^8$ have a total of from 4 to 7 ring carbon atoms.
12. A compound of claim 1 in which n is 0.
13. A compound of claim 1 in which n is 1.
14. A compound of claim 13 in which each of $R^2$ and $R^3$ is a hydrogen atom.
15. A compound of claim 2 or 10 in which Z has the structure:

$$-(CH_2)_p-$$

in which p is a whole integer of from 2 to 6.
16. A compound of claim 1 in which M is a hydrolyzable or saponifiable radical.
17. A compound of claim 1 in which M is a hydrogen atom.
18. A compound of claim 1 in which M is a cation.
19. The compound of claim 16 which is ethyl 4-(4,4-dimethyl-4-sila-n-tetradecylamino)-benzoate.
20. The compound of claim 16 which is ethyl 4-(4,4-dimethyl-4-sila-n-hexadecylamino)-benzoate.
21. The compound of claim 16 which is ethyl 4-(5,5-dimethyl-5-sila-n-hexadecylamino)-benzoate.

22. The compound of claim 16 which is ethyl 4-(6,6-dimethyl-6-sila-n-hexadecylamino)-benzoate.

23. The compound of claim 17 which is 4-(4,4-dimethyl-4-sila-n-tetradecylamino)-benzoic acid.

24. The compound of claim 17 which is 4-(4,4-dimethyl-4-sila-n-hexadecylamino)-benzoic acid.

25. The compound of claim 17 which is 4-(5,5-dimethyl-5-sila-n-hexadecylamino)-benzoic acid.

26. The compound of claim 17 which is 4-(6,6-dimethyl-6-sila-n-hexadecylamino)-benzoic acid.

27. The compound of claim 18 which is sodium 4-(4,4-dimethyl-4-sila-n-tetradecylamino)-benzoate.

28. The compound of claim 18 which is sodium 4-(4,4-dimethyl-4-sila-n-hexadecylamino)-benzoate.

29. The compound of claim 18 which is sodium 4-(5,5-dimethyl-5-sila-n-hexadecylamino)-benzoate.

30. The compound of claim 18 which is sodium 4-(6,6-dimethyl-6-sila-n-hexadecylamino)-benzoate.

31. The compound of claim 18 which is sodium 4-(4,4-diphenyl-sila-n-pentylamino)-benzoate.

32. The compound of claim 18 which is sodium 4-(4-phenyl-4-methyl-4-sila-n-pentylamino)-benzoate.

33. The compound of claim 18 which is sodium 4-(4-phenoxyphenyl-4-methyl-4-sila-n-pentylamino)-benzoate.

34. A pharmaceutical composition in unit dose form for treating or preventing atherosclerosis in a mammal comprising an anti-atherosclerotic-effective amount of a compound of claim 1 and a non-toxic pharmaceutically-acceptable carrier.

35. A method of treating or preventing atherosclerosis in a mammal, comprising administering an antiatherosclerotic-effective amount of a compound of claim 1 to said mammal.

* * * * *